US012691211B2

(12) United States Patent
Omar

(10) Patent No.: US 12,691,211 B2
(45) Date of Patent: Jul. 28, 2026

(54) DEVICES, SYSTEMS, AND METHODS FACILITATING FLUID-ASSISTED SURGICAL TISSUE TREATMENT

(71) Applicant: Medtronic Xomed, LLC, Jacksonville, FL (US)

(72) Inventor: Mansur I. Omar, Jacksonville, FL (US)

(73) Assignee: Medtronic Xomed, LLC, Minneapolis, MN (US)

( * ) Notice: Subject to any disclaimer, the term of this patent is extended or adjusted under 35 U.S.C. 154(b) by 701 days.

(21) Appl. No.: 18/112,054

(22) Filed: Feb. 21, 2023

(65) Prior Publication Data

US 2023/0302215 A1 Sep. 28, 2023

Related U.S. Application Data

(60) Provisional application No. 63/322,829, filed on Mar. 23, 2022.

(51) Int. Cl.
*A61M 1/00* (2006.01)

(52) U.S. Cl.
CPC ................ *A61M 1/74* (2021.05); *A61M 1/72* (2021.05); *A61M 1/73* (2021.05); *A61M 1/774* (2021.05); *A61M 2205/332* (2013.01); *A61M 2205/3592* (2013.01); *A61M 2205/502* (2013.01)

(58) Field of Classification Search
CPC ........... A61M 1/72; A61M 1/74; A61M 1/77; A61M 1/774; A61M 3/0201
See application file for complete search history.

(56) References Cited

U.S. PATENT DOCUMENTS 1,071,688 A * 9/1913 Bono ..................... A44B 99/00
24/351
5,573,515 A * 11/1996 Wilson .............. A61M 5/14216
604/152

(Continued)

FOREIGN PATENT DOCUMENTS

EP 2331161 B1 12/2014

OTHER PUBLICATIONS

EESR 23161650.9 dated Jul. 7, 2023; 10pp.

*Primary Examiner* — Scott J Medway
(74) *Attorney, Agent, or Firm* — Carter, DeLuca & Farrell LLP

(57) ABSTRACT

A cassette and remote control assembly includes a cassette, a remote control attachment, and an electrical connector. The cassette includes a fluid line coupled between a fluid input and a fluid output and is configured to couple to a console to enable pumping of fluid along the fluid line. The cassette also includes an electronics board configured to communicate with the console. The remote control attachment is configured to releasably attach to a handpiece of a surgical device and includes at least one sensor configured to sense at least one property of the handpiece, a user input interface configured to receive a clinician input, and/or an output device configured to output an indicator. The electrical connector connects the remote control attachment with the cassette, thereby electrically coupling the electronics board of the cassette with the sensor, the user input interface, and/or the output device of the remote control attachment.

18 Claims, 7 Drawing Sheets

(56)                References Cited

U.S. PATENT DOCUMENTS

| | | | | |
|---|---|---|---|---|
| 5,685,821 A * | 11/1997 | Pike | A61B 1/0004 | 604/35 |
| 5,733,256 A * | 3/1998 | Costin | A61F 9/00745 | 604/35 |
| 5,800,383 A * | 9/1998 | Chandler | A61M 31/00 | 604/35 |
| 5,807,075 A * | 9/1998 | Jacobsen | A61M 5/142 | 417/313 |
| 5,810,770 A * | 9/1998 | Chin | A61M 3/0202 | 604/65 |
| 6,535,689 B2 * | 3/2003 | Augustine | A61M 5/44 | 392/470 |
| 6,997,942 B2 * | 2/2006 | Machold | A61F 7/123 | 607/104 |
| 7,883,458 B2 * | 2/2011 | Hamel | A61B 90/70 | 600/101 |
| 8,852,085 B2 | 10/2014 | Shener-Irmakoglu et al. | | |
| 9,295,765 B2 * | 3/2016 | Muri | A61M 3/0201 | |
| 9,770,541 B2 | 9/2017 | Carr et al. | | |
| 11,191,528 B2 * | 12/2021 | Bucina | A61B 17/1626 | |
| 2003/0212379 A1 * | 11/2003 | Bylund | G16H 20/17 | 700/282 |
| 2007/0107490 A1 * | 5/2007 | Artsyukhovich | A61M 1/77 | 73/1.16 |
| 2007/0161978 A1 * | 7/2007 | Fedenia | A61M 1/77 | 606/34 |
| 2008/0097284 A1 | 4/2008 | Gao et al. | | |
| 2010/0049119 A1 * | 2/2010 | Norman | A61M 3/0202 | 604/31 |
| 2011/0190690 A1 | 8/2011 | Humayun et al. | | |
| 2014/0266636 A1 * | 9/2014 | Larsen | G08C 19/16 | 340/12.5 |
| 2015/0265259 A1 * | 9/2015 | Regere | A61C 17/0202 | 700/275 |
| 2017/0224429 A1 * | 8/2017 | Fung | A61B 90/08 | |
| 2020/0405311 A1 * | 12/2020 | Shelton, IV | G06K 19/07758 | |
| 2024/0009371 A1 * | 1/2024 | Patrinicola | A61M 1/74 | |

* cited by examiner

DEVICES, SYSTEMS, AND METHODS FACILITATING FLUID-ASSISTED SURGICAL TISSUE TREATMENT

CROSS REFERENCE TO RELATED APPLICATION

This application claims the benefit of and priority to U.S. Provisional Patent Application No. 63/322,829, filed on Mar. 23, 2022, the entire contents of which are hereby incorporated herein by reference.

FIELD

The present disclosure relates to surgical devices, systems, and methods and, more specifically, to powered, fluid-assisted surgical devices, systems, and methods.

BACKGROUND

Fluid is utilized in conjunction with many powered surgical devices, systems, and methods to facilitate performing a surgical task such as, for example, enabling irrigation at a treatment site, aspiration at a treatment site, cleaning of a surgical device, washing of a treatment site, clearing a field of view, cooling a surgical device, etc. Some non-limiting examples of surgical devices that may benefit from the use of fluid include microdebriders, surgical drills, surgical saws, suction irrigators, tissue shavers, endoscopes, balloon or other catheters, energy devices, and the like.

Powered surgical systems typically include a console connected to a surgical device to power and control the surgical device. Such consoles may further connect to a fluid source and/or fluid collection canister and incorporate a pump to enable control of the flow of fluid to and/or from the surgical site.

SUMMARY

The terms "about," substantially," and the like, as utilized herein, are meant to account for manufacturing, material, environmental, use, and/or measurement tolerances and variations, and in any event may encompass differences of up to 10%. Further, to the extent consistent, any of the aspects described herein may be used in conjunction with any or all of the other aspects described herein.

Provided in accordance with aspects of the present disclosure is a fluid cassette and remote control assembly including a cassette, a remote control attachment, and an electrical connector. The cassette includes at least one fluid line configured to operably couple between at least one fluid input and at least one fluid output. The cassette is configured to operably couple to a console to enable pumping of fluid, e.g., sterile fluid, along the at least one fluid line. The cassette further includes an electronics board configured to wirelessly communicate with the console when the cassette is engaged with the console. In other aspects, the electronics board of the cassette is configured to communicate the console via a wired (physical contact-based connection. The remote control attachment is configured to releasably attach to a handpiece of a surgical device and includes at least one sensor configured to sense at least one property of the handpiece, a user input interface configured to receive an input from a clinician, and/or an output device configured to output an indicator (e.g., an audible tone, visual indicator, etc.) to a clinician. The electrical connector connects the remote control attachment with the cassette, thereby electrically coupling the electronics board of the cassette with the at least one sensor, user input interface, and/or output device of the remote control attachment.

In an aspect of the present disclosure, the sensor is an inertial measurement sensor. The inertial measurement sensor may include an accelerometer configured to sense movement of the handpiece, a gyroscope configured to sense orientation of the handpiece, and/or a magnetometer configured to sense activation of the handpiece.

In another aspect of the present disclosure, the user input interface is configured to sense a finger gesture input to a surface thereof. In such aspects, the user input interface may be configured to receive a finger gesture input on the surface thereof to control operation of the surgical device and/or pumping of the fluid along the at least one fluid line. This control is enabled by the wireless (and/or wired) communication interface between the electronics board and the console.

In still another aspect of the present disclosure, the output device is configured to provide at least one of an audible output or a visual output. In such aspects, the output device may be configured to provide an output signal generated by the console and communicated to the remote control attachment via the wireless (and/or wired) communication interface between the electronics board and the console.

In yet another aspect of the present disclosure, the console can transmit and the electronics board within the cassette can be configured to wirelessly receive power from the console to power the electronics board and the remote control attachment.

In still yet another aspect of the present disclosure, the cassette further includes a user input sensor disposed thereon and electrically connected to the electronics board for relaying sensed user inputs to the console via the wireless (and/or wired) communication interface between the electronics board and the console. In such aspects, in response to the user input sensor sensing a user input, the electronics board may be configured to wirelessly (and/or via a wired connection) send an eject cartridge input signal to the console to release the cartridge.

In another aspect of the present disclosure, tubing is connected to the at least one fluid output of the cassette at a first end and is configured to connect to the surgical device at a second end. The tubing and the electrical connector may be bundled with one another along portions of lengths thereof.

A surgical system provided in accordance with aspects of the present disclosure includes a console, a surgical device, and a fluid cassette and remote control assembly. The console includes at least one surgical device port, at least one cassette bay, a first or console electronics board, and pump components. The first electronics board and the pump components are operably positioned relative to the at least one cassette bay. The surgical device is configured to connect to the console via the at least one surgical device port and includes a handpiece and an end effector. The fluid cassette and remote control assembly includes a cassette, a remote control attachment, and an electrical connector. In aspects, the fluid cassette and remote control assembly further includes a tubing set incorporating the electrical connector. The cassette is configured for receipt within the at least one cassette bay and includes a second or cassette electronics board and at least one fluid line configured to operably couple between at least one fluid input and at least one fluid output. When the cassette is received within the at least one cassette bay, the cassette is configured to operably couple to the pump components of the console to enable pumping of fluid along the at least one fluid line and the first (console) and second (cassette) electronics boards are configured to wirelessly (and/or via a wired connection) communicate with one another. The remote control attachment is configured to releasably attach to the handpiece of the surgical device and includes a sensor configured to sense a property of the handpiece, a user input interface configured to receive an input from a clinician, and/or an output device configured to output an indicator (audible, visual, etc.)_ to a clinician. The electrical connector connects the remote control attachment with the cassette to electrically couple the second electronics board with the sensor, user input interface, and/or output device, thereby wirelessly (and/or via a wired connection) coupling the first electronics board with the sensor, user input interface, and/or output device when the cassette is received within the at least one cassette bay.

In an aspect of the present disclosure the sensor is an inertial measurement sensor including at least one of an accelerometer configured to sense movement of the handpiece, a gyroscope configured to sense orientation of the handpiece, or a magnetometer configured to sense activation of the handpiece.

In another aspect of the present disclosure, the user input interface is configured to receive a finger input on a surface thereof to control at least one of operation of the surgical device or pumping of fluid along the at least one fluid line via the wireless (and/or wired) communication interface between the first and second electronics boards.

In yet another aspect of the present disclosure, the output device is configured to provide at least one of an audible output or a visual output generated by the console and communicated to the remote control attachment via the wireless (and/or wired) communication interface between the first and second electronics boards.

In still another aspect of the present disclosure, the first electronics board is configured to wirelessly transfer power to the second electronics board to power the second electronics board and the remote control attachment.

In still yet another aspect of the present disclosure, the cassette further includes a user input sensor disposed thereon and electrically connected to the second electronics board for relaying sensed user inputs to the console via the wireless (and/or wired) communication interface between the first and second electronics boards. In such aspects, in response to the user input sensor sensing a user input, the second electronics board wirelessly (or via a wired connection) sends a cartridge eject signal to the first electronics board to disengage the pump components of the console.

In another aspect of the present disclosure, tubing is connected to the at least one fluid output of the cartridge at a first end and configured to connect to the surgical instrument at a second end. The tubing and the electrical connector may be bundled with one another (and electrically isolated) along portions of lengths thereof.

BRIEF DESCRIPTION OF THE DRAWINGS

Various aspects and features of the present disclosure are described hereinbelow with reference to the drawings wherein.

DETAILED DESCRIPTION

Figures 1, 2:
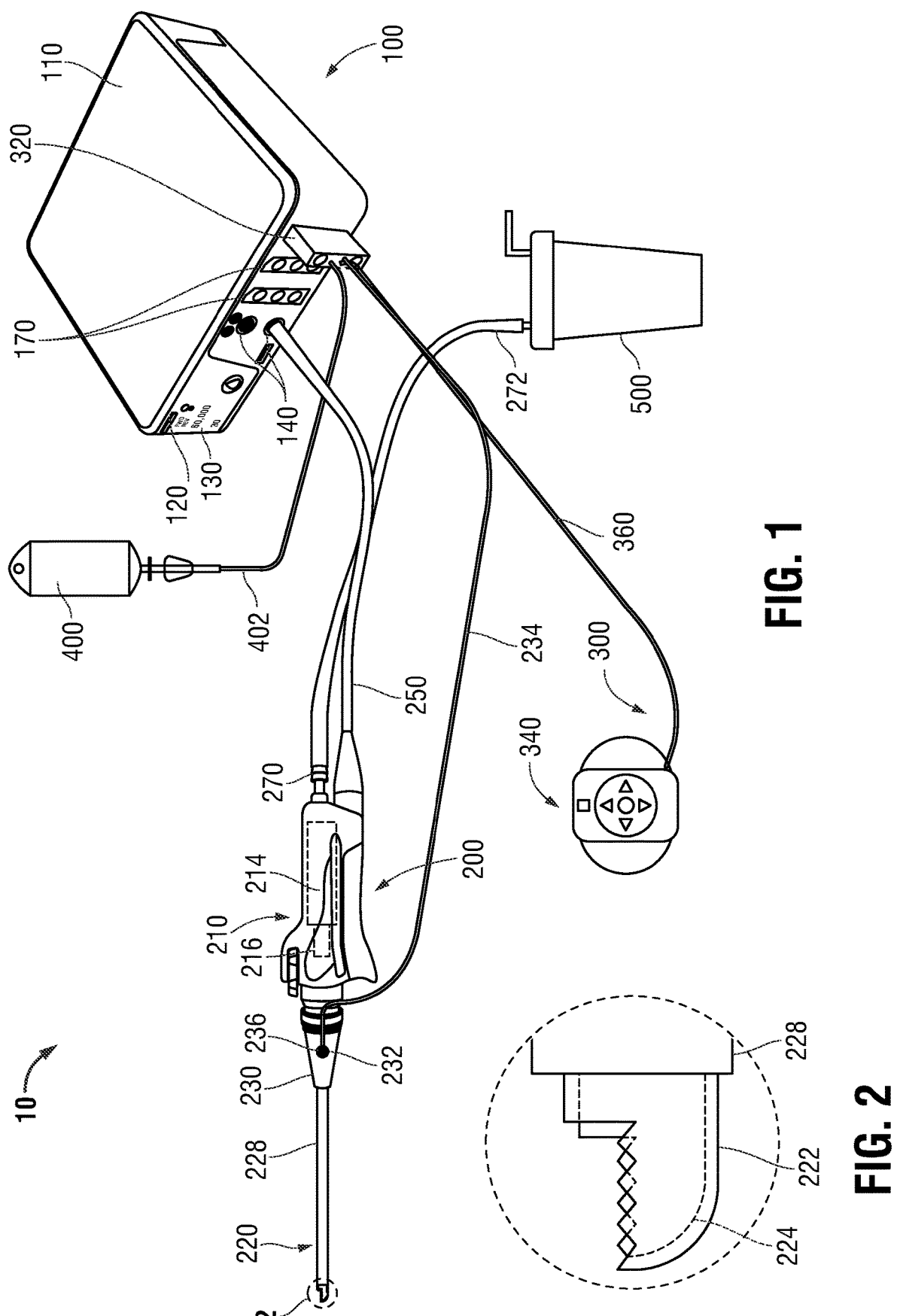
FIG. 1 is a perspective view of a surgical system provided in accordance with aspects of the present disclosure including a surgical device, a console, and a fluid cassette and remote control assembly operably coupling the surgical device and console with one another, wherein the surgical system is shown further including a fluid source and a fluid collection canister.
FIG. 2 is an enlarged, perspective view of the indicated area of detail of FIG. 1.

Referring to FIG. 1, a surgical system 10 provided in accordance with the present disclosure generally includes: a console 100; one or more surgical devices 200 configured to be powered, controlled, energized, supplied fluid, and/or supplied vacuum by console 100; one or more fluid cassette and remote control assemblies 300 each operably coupling console 100 with one of the surgical devices 200; one or more fluid sources 400; and/or one or more fluid collection canisters 500. Although plural surgical devices 200, fluid cassette and remote control assemblies 300, fluid sources 400, and/or fluid collection canisters 500 are contemplated, surgical system 10 is described below with reference to only one of each of these features for the purposes of brevity and understanding. Likewise, although console 100 may include plural identical or similar features to accommodate, for example, the plurality of surgical devices 200, fluid cassette and remote control assemblies 300, fluid sources 400, and/or fluid collection canisters 500, each of these features is described in the singular hereinbelow for the purposes of brevity and understanding.

Console 100 includes: a housing 110; a power button 120; a graphical user interface (GUI) 130 (such as, for example, a touch screen GUI); one or more ports 140 such as, for example, power ports for powering and controlling connected powered surgical device(s) e.g., surgical device 200, energy ports for providing surgical energy, e.g., monopolar, bipolar, microwave, ultrasonic, thermal, light, and/or other surgical energy, to connected energy device(s), additional ports 160 for connection of one or more auxiliary devices such as a foot switch; and a plurality of cassette bays 170. Console 100 further includes one or more central processing units (CPU's) and/or microcontroller units (MCU's), power generating and control hardware, surgical energy generating and control hardware, and/or any other suitable hardware and corresponding firmware/software stored thereon for operating and controlling operation of surgical devices 200 connected thereto.

Figure 3:
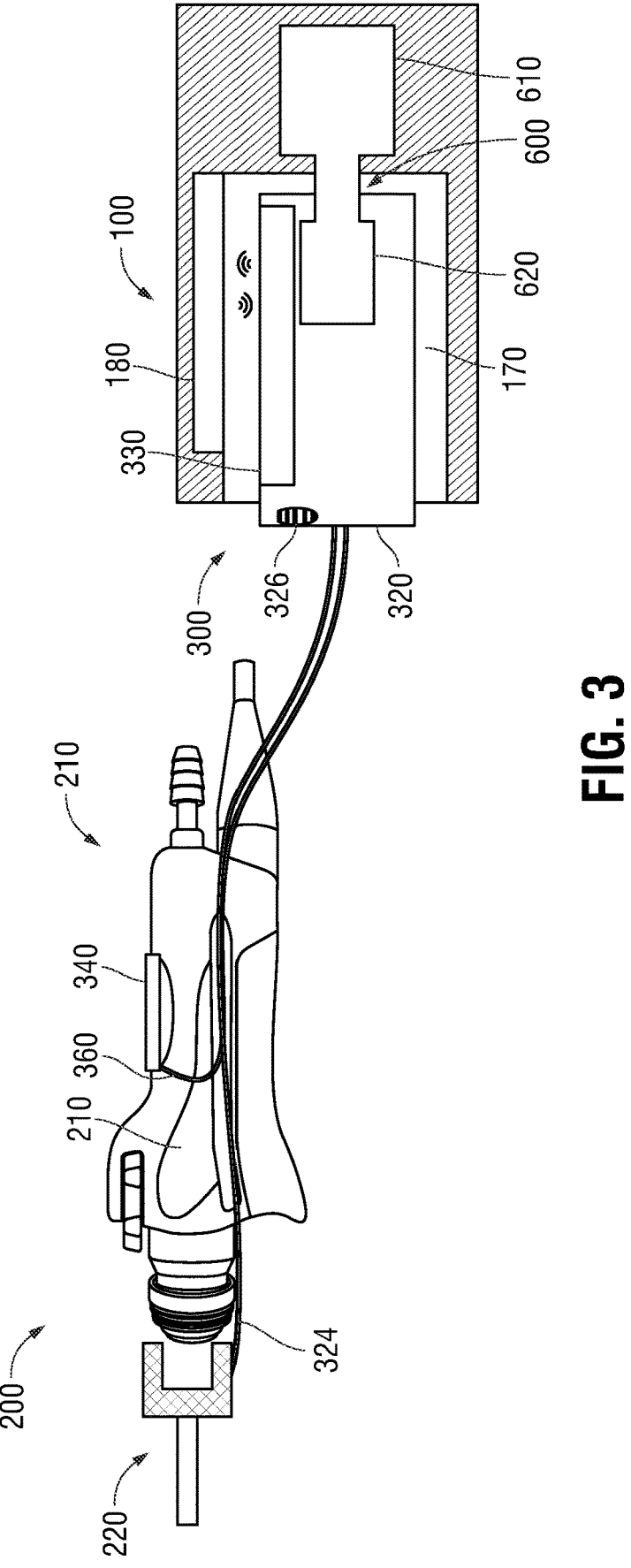
FIG. 3 is a schematic illustration showing the fluid cassette and remote control assembly operably coupling the surgical device and console with one another.

Console 100 additionally includes a first portion 610 of a pump 600 (see FIGS. 3 and 4A) disposed therein and operably positioned relative to a corresponding cassette bay 170 to operably interface with a second portion 620 of pump 600 (see FIGS. 3 and 4A) of cassette 320 of fluid cassette and remote control assembly 300 to enable the selective pumping of fluid through cassette 320 to selectively deliver fluid to surgical device 200 when cassette 320 is received within cassette bay 170. One of the CPU's and/or MCU's of console 100 may also control first portion 610 of pump 600 (FIGS. 3 and 4A) according to a particular control program selected (e.g., via GUI 130), according to user actuation of one or more controls associated with remote control attachment 340 of fluid cassette and remote control assembly 300, in response to sensed feedback, and/or in any other suitable manner.

First portion 610 of pump 600 (FIGS. 3 and 4A) may include, for example, pump drive hardware e.g., a stepper motor, and drive train configured to operably interface with a complementarily positioned peristaltic pump head and fluid line 612 (thus defining second portion 620 of pump 600 (FIGS. 3 and 4A)) of cassette 320 of fluid cassette and remote control assembly 300 such that first and second portions 610, 620 cooperate to define a peristaltic pump. In peristaltic pump configurations, the fluid line 612 that interfaces with the peristaltic pump head may be divided downstream of the peristaltic pump to provide multiple fluid lines 612 for selective and independent output of pumped fluid.

In other configurations, first portion 610 may include a pump drive actuator, e.g., a rotary actuator, configured to drive a pump head having one or more fluid lines 612 connected thereto (thus defining second portion 620 of pump 600 (FIGS. 3 and 4A)) of cassette 320 of fluid cassette and remote control assembly 300 such that portions 610, 620 cooperate to define a rotary pump. In these and other aspects where multiple fluid lines 612 (or multiple outputs from a divided fluid line 612) are provided, first portion 610 of pump 600 (FIGS. 3 and 4A) may include one or more valve actuators (e.g., solenoid driven valve actuators), to enable the fluid lines 612 to be selectively and independently pinched closed, thereby selectively and independently controlling fluid flow along multiple flow paths. Such a configuration suitable for use in accordance with the present disclosure is detailed in U.S. patent application Ser. No. 17/549,758, filed on Dec. 13, 2021 and titled "SURGICAL DEVICES, SYSTEMS, AND METHODS FACILITATING MULTIPLE FLOW PATH FLUID MANAGEMENT," the entire contents of which are hereby incorporated herein by reference. Other suitable configurations of pump 600 are also contemplated. Further, regardless of the particular configuration of pump 600, pump 600 enables the selective pumping of fluid from the fluid source 400 to surgical device 200 (and/or otherwise to/from a surgical site and/or other surgical devices) via cassette 320.

Continuing with reference to FIG. 1, surgical device 200, as noted above, may be powered, controlled, energized, supplied fluid, and/or supplied vacuum by console 100. Surgical device 200 may be configured as, for example and without limitation, one or more of a microdebrider, surgical drill, surgical saw, suction irrigator, tissue shaver, endoscope, sheath for an endoscope (e.g., a lens cleaning sheath), balloon or other catheter, energy device, fluid cooled device, etc.

In aspects, surgical device 200 includes a handpiece 210 and an end effector 220 releasably engagable with handpiece 210. More specifically, with respect to surgical tissue removal devices, e.g., microdebriders, surgical drills, tissue shavers, etc., handpiece 210 may include a motor 214 disposed therein and a drive rotor 216 coupled to motor 214 and configured to drive a movable (e.g., rotational, reciprocating, oscillating, or combinations thereof) component of end effector 220 to remove tissue from a surgical site. As shown in FIG. 2, for example, end effector 220 may include an outer shaft 222 and an inner shaft 224 configured to be driven by motor 214 via drive rotor 216 to move relative to outer shaft 222 to cut tissue. Further, vacuum may be applied through outer shaft 222 and/or inner shaft 224 to remove the cut tissue (along with fluid and debris) from the surgical site through outer shaft 222 and/or inner shaft 224 and to fluid collection canister 500. Surgical device 200 may also include a power cord 250 configured to connect surgical device 200 to console 100 to power and control the motor, thereby controlling operation of end effector 220.

End effector 220 may additionally or alternatively include a sheath 228 disposed about (in fixed or removable fashion) outer shaft 222 and configured to deliver fluid to the surgical site. In such aspects, a proximal hub 230 disposed at the proximal end of sheath 228 may include a port 232 to connect to an inflow fluid line 234 (e.g., tube) to enable fluid to be pumped through sheath 228 and into the surgical site. Alternatively, port 232 may enable connection of a vacuum line such that sheath 228 may be used for withdrawing fluid from the surgical site. Other suitable configurations of surgical device 200 for treating tissue and/or of fluid supply/removal associated with surgical device 200 are also contemplated.

Referring back to FIG. 1, fluid source 400, e.g., an IV fluid bag, is fluidly coupled to one or more fluid flow paths defined within cassette 320 of fluid cassette and remote control assembly 300, e.g., via a fluid line 402 connected to one of one or more inflow ports 324a of cassette 320. Cassette 320 further includes one or more outflow ports 324b to enable a fluid line 234 to connect the outflow of cassette 320 to port 232 of proximal hub 230 of end effector 220 of surgical device 200 to enable the supply of fluid to (or withdrawal of fluid from) sheath 228. Cassette 320 and console 100, as noted above, cooperate to define a pump 600 (FIGS. 3 and 4A) to enable the pumping of fluid from fluid source 400 to end effector 220 of surgical device 200 when cassette 320 is received within cassette bay 170 of console 100.

Fluid collection canister 500, in aspects where provided, is fluidly coupled to an outflow port 270 of surgical device 200 via a fluid line 272 and, in aspects, is further coupled to a vacuum source to facilitate the withdrawal of fluid (and tissue, debris, etc.) from the surgical site, through surgical device 200, and into fluid collection canister 500.

Referring to FIGS. 3-6, fluid cassette and remote control assembly 300 includes a cassette 320, a remote control attachment 340, an electrical connector 360 (e.g., a cable) connecting remote control attachment 340 with cassette 320, and a fluid line 234 including a fluid connector 236 disposed at the free end thereof and configured to connect to port 232 of proximal hub 230 of end effector 220 of surgical device 200 (or an inflow port of any other suitable surgical device). Fluid line 234 may be integrally connected to cassette 320 or may be removable therefrom. In aspects, fluid line 234 and electrical connector 360 are bundled along at portions of the lengths thereof, e.g., adhered to one another, disposed within a common sheath, etc.

Cassette 320 includes an outer housing 322 housing the internal operable components of cassette 320 therein including the one or more fluid lines 612, second portion 620 of pump 600, and an electronics circuit board or electronics board 330. Outer housing 322 further supports a user interface sensor 326 thereon such as, for example, a force sensor, a touch sensor, etc. configured to sense one or more user inputs, e.g., force applied, touches, patterns, etc. Further, outer housing 322 includes one or more inflow port 324a to enable connection of fluid source 400, e.g., via a fluid line 402, with the one or more of fluid lines 612; one or more outflow ports 324b to enable connection of the one or more fluid lines 612 with corresponding fluid lines, e.g., fluid line 234, to enable pump 600 to pump fluid along the one or more fluid lines 612 and through fluid line 234 to surgical device 200; and an electrical port 324c configured to integrally or removable connect electrical connector 360 with electronics board 330, thereby connecting electronics board 330 with remote control attachment 340. In aspects, cassette 320 further includes a flow sensor 329, e.g., an infrared flow sensor or an ultrasonic flow sensor, operably positioned relative to each fluid line 612 to enable detection of fluid flow therethrough and, in aspects, a rate of fluid flow.

Electronics board 330 includes a communication antenna 331, communication circuitry 332, power management and energy harvesting circuitry 333, power output circuitry 334, an input/output (I/O) 335, a processor 336 (including a memory storing instructions for use therewith), and a memory 337 (e.g., an SRAM, EEPROM, or other suitable memory or combinations of memories capable of storing identifying information, use information, and/or setting information relating to cassette 320 and, in aspects, which may be password protected and/or encrypted). As detailed below, electronics board 330 is configured to wirelessly interface with an electronics board 180 of console 100 including a communication antenna 181, communication circuitry 182, an application processor 186 (including a memory storing instructions for use therewith), and a power supply 188. Alternatively or additionally, electronics board 330 may be configured for wired (e.g., via physically engaged or abutting electrical contacts) interfacing with electronics board 180 of console 100, as detailed below with reference to FIG. 4B. Console 100 further includes first portion 610 of pump 600 (as noted above) disposed in electrical communication with electronics board 180. First portion 610 of pump 600, together with second portion 620 of pump 600, as detailed above, enables the pumping of fluid from cassette 320 to surgical device 200.

Figure 4A:
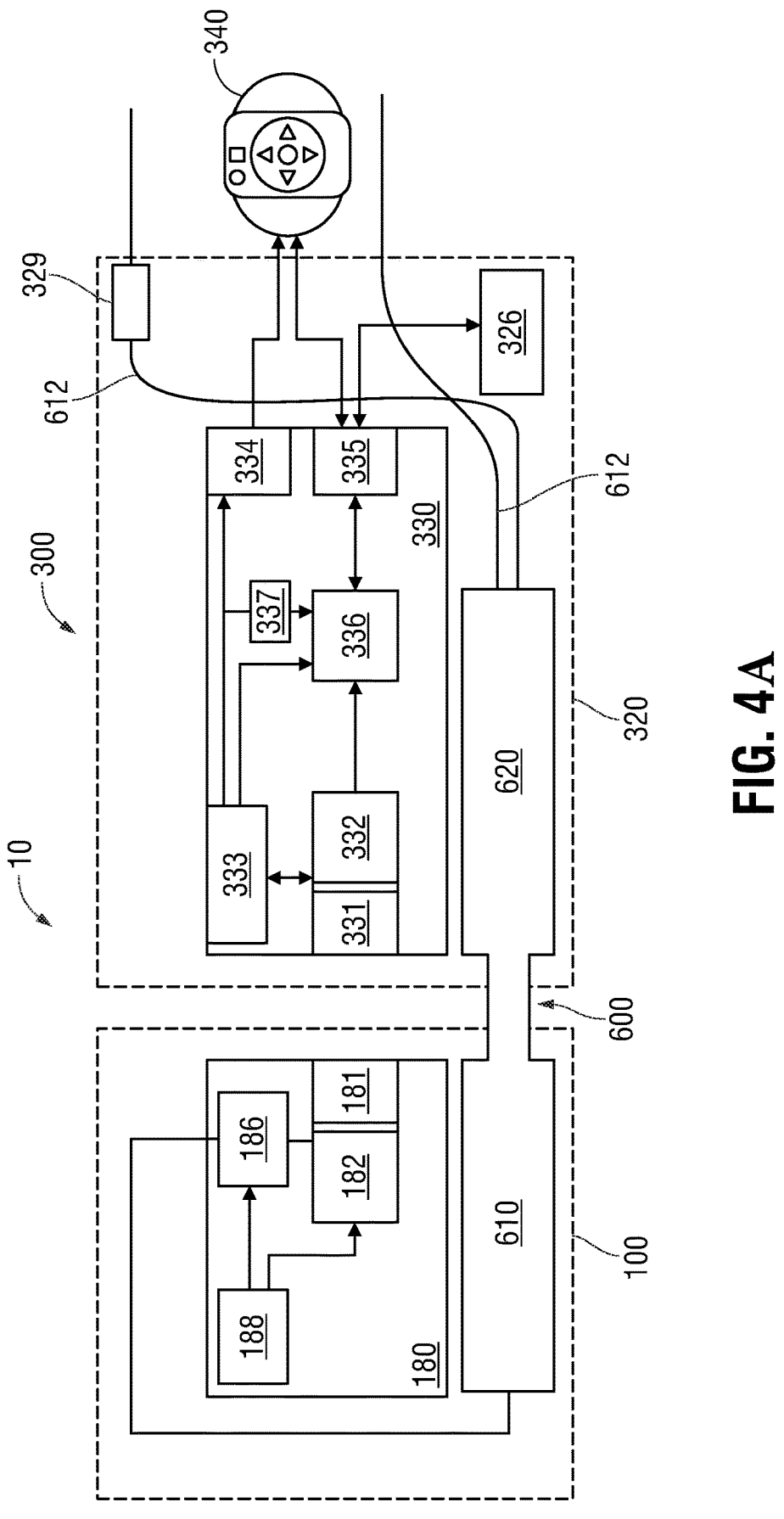
FIG. 4A is a block diagram illustrating the fluid cassette and remote control assembly interfacing with the console.
Figure 4B:
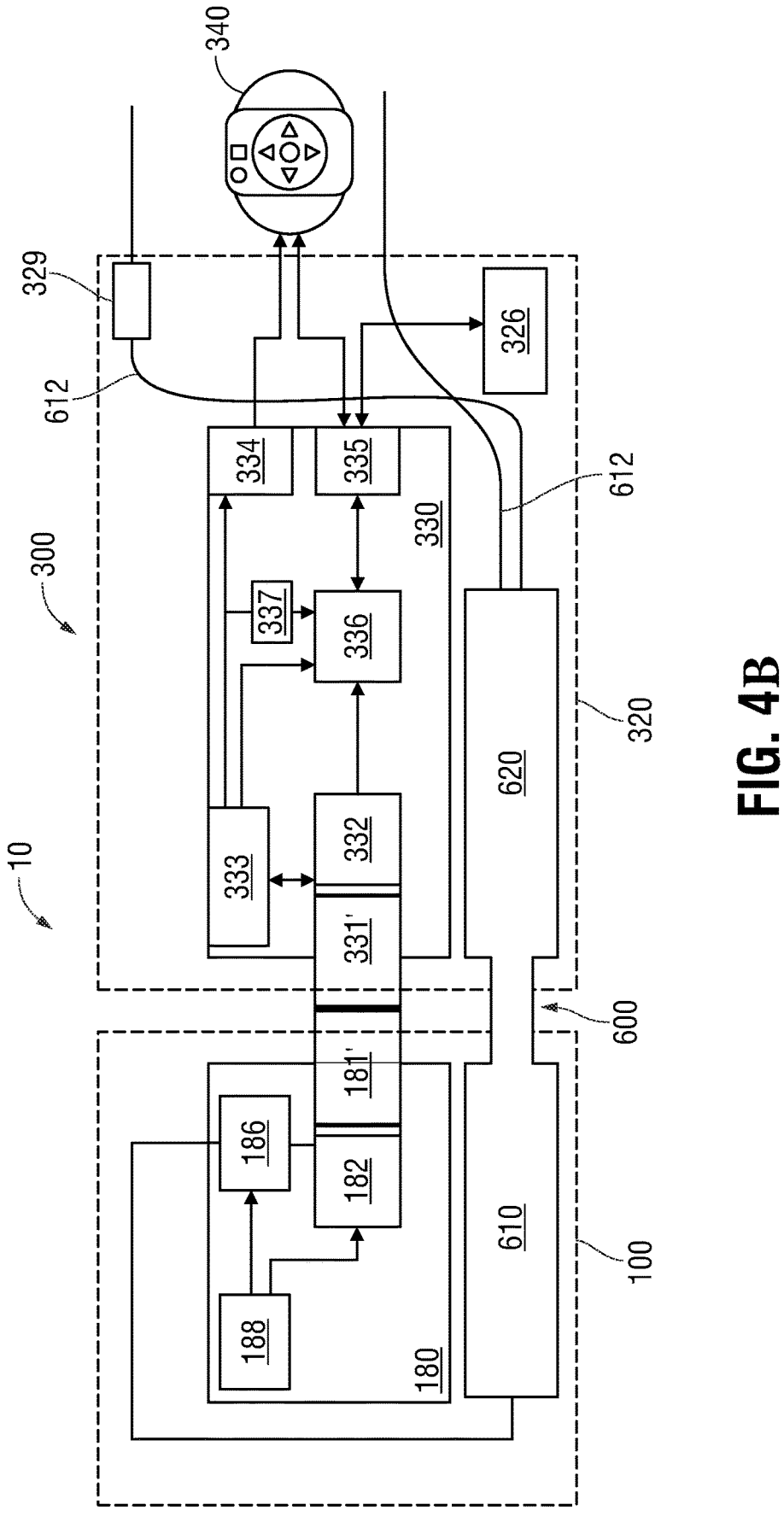
FIG. 4B is a block diagram illustrating another configuration of the fluid cassette and remote control assembly interfacing with the console.
Figures 5, 6:
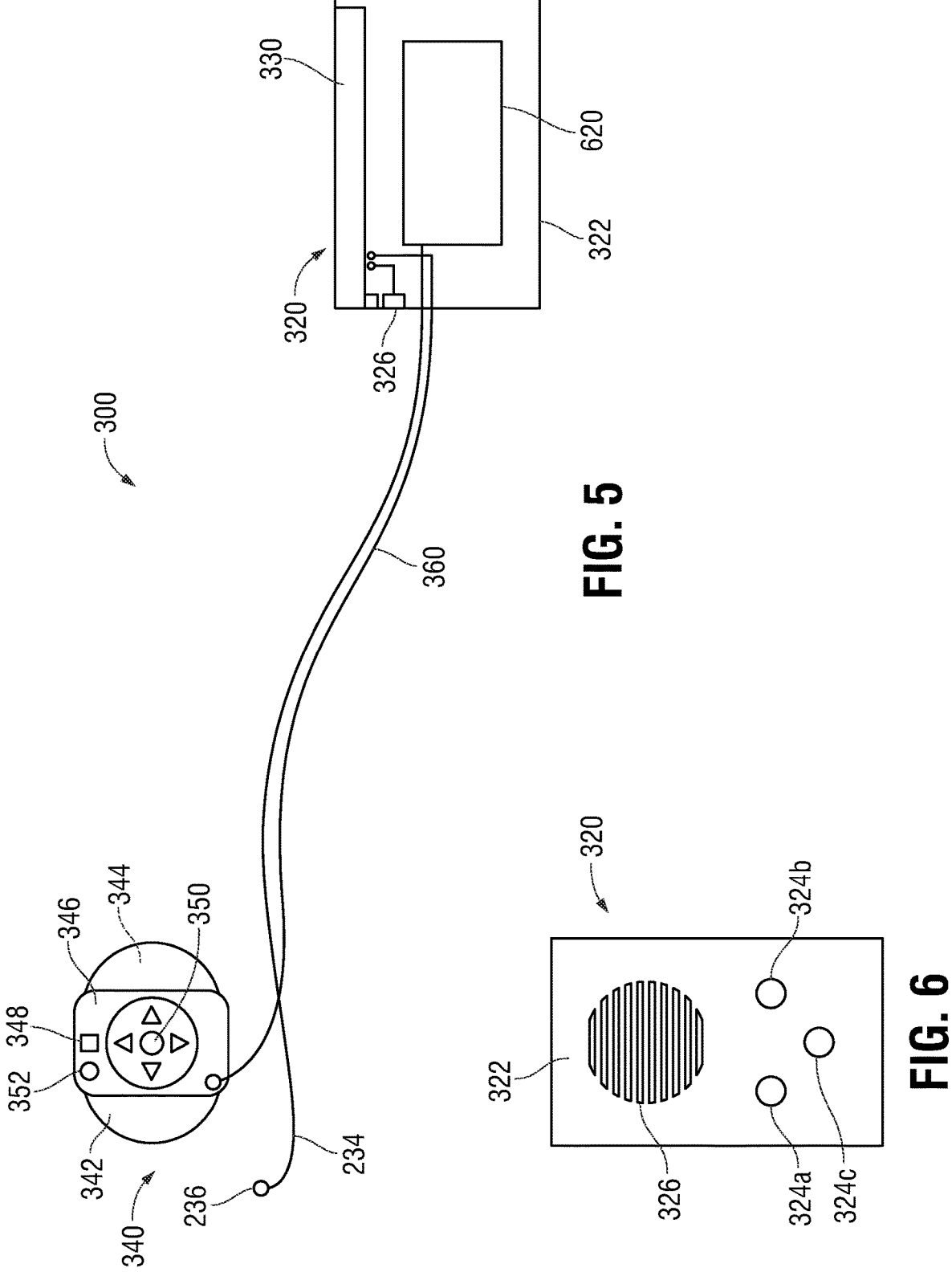
FIG. 5 is a schematic illustration of the fluid cassette and remote control assembly.
FIG. 6 is a front view of the cassette of the fluid cassette and remote control assembly.
Figures 7, 8:
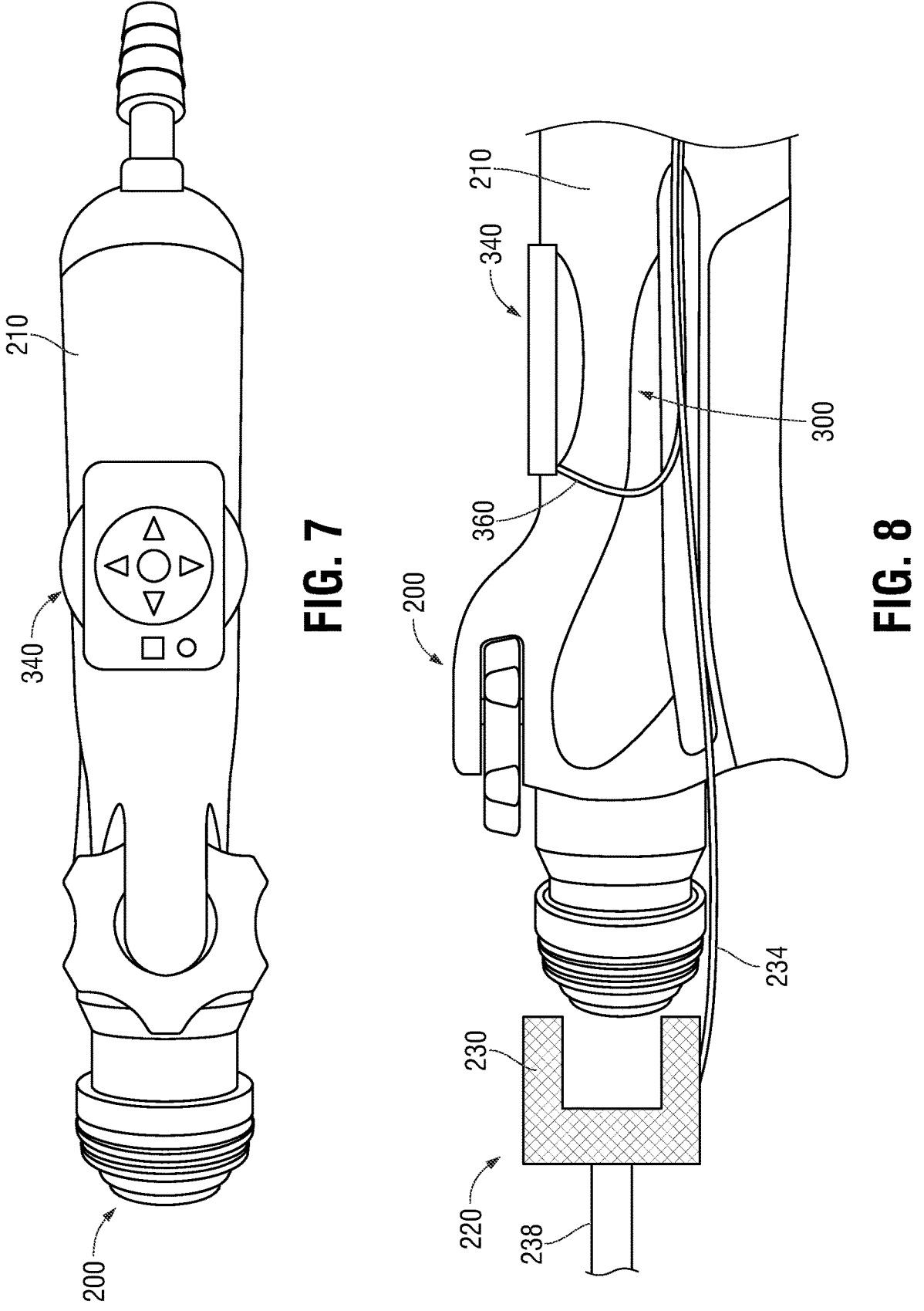
FIG. 7 is a top view of a handpiece of the surgical device including a remote control attachment of the fluid cassette and remote control assembly disposed thereon.
FIG. 8 is a side, exploded view of the handpiece and a tool assembly of the surgical device, including the fluid cassette and remote control assembly operably coupled thereto.
Figure 9:
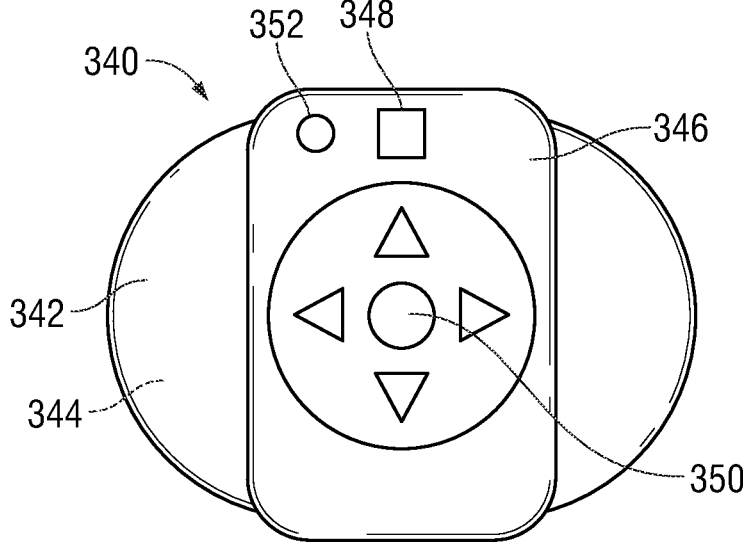
FIG. 9 is a top view of the remote control attachment.

With particular reference to FIG. 4A, communication antenna 331 and communication circuitry 332 of electronics board 330 of cassette 320 are configured for wireless communication with communication antenna 181 and communication circuitry 182 of electronics board 180 of console 100 when cassette 320 is received within cassette bay 170. More specifically, antennae 331, 181 may be near field communication (NFC) antennae 331, 181 enabling wireless radio frequency (RF) communication of power and data signals therebetween, although other suitable wireless communication configurations are also contemplated. With momentary reference to FIG. 4B, with respect to wired connections, rather than antennae 331, 181 (FIG. 4A; or, in addition to antennae 331, 181 (FIG. 4A) in aspects where both wired and wireless communication are provided), communication circuitry 332 and communication circuitry 182 include electrical contact assemblies 331', 181' (each including one or more electrical contacts) that are configured to physically contact one another when cassette 320 is received within cassette bay 170 to thereby establish wired electrical communication therebetween and enabling communication of power and data signals therebetween. In aspects, power transfer may be provided via wired communication while data is transferred via wireless communication, although other configurations including either or combinations of wireless and wired communication are also contemplated.

Turning back to FIG. 4A, with respect to wireless power transfer, power from power supply 188 of electronics board 180 of console 100 is wirelessly communicated from communication antenna 181 of electronics board 180 to communication antenna 331 of electronics board 330 to enable powering of power management and energy harvesting circuitry 333 of electronics board 330 which, in turn, distributes power to power the various components of electronics board 330 as well as user interface sensor 326 and remote control attachment 340. In this manner, the fluid cassette and remote control assembly 300 is powered wirelessly from console 100 (and independently of the cabled connection of surgical device 200 with console 100).

With respect to wireless data transfer, communication antennae 181, 331 and communication circuitry 182, 332 enable bidirectional wireless data communication between application processor 186 of electronics board 180 of console 100 (which, in turn, communicates with first portion 610 of pump 600) and processor 336 of electronics board 330 of cassette 320 (which, in turn, communicates with user interface sensor 326 and remote control attachment 340 via I/O 335), respectively. This bidirectional wireless data communication enables console 100 to identify cassette 320 (e.g., by unique ID, device type, lot number, manufacture date, etc.), for example, to determine or retrieve configuration data, features, components, and/or settings associated with cassette 320 to facilitate configuring console 100 for use therewith; to authenticate cassette 320 (e.g., to prevent counterfeit or unverified cassettes 320 from being used); and to read/write use information to/from cassette 320 (e.g., a use count, that the cassette has been used, etc.). In aspects, fluid cassette and remote control assembly 300 is configured as a single use (or limited use) disposable component such that console 100 writes to a cassette 320 to active a used flag after a use thereof and inhibits use of a cassette 320 that has its used flag activated. Console 100 and surgical device 200 (FIGS. 1 and 3) may be configured as reusable components.

The bidirectional wireless data communication between console 100 and cassette 320 also enables feedback signals, e.g., based upon sensor data obtained at remote control attachment 340, and/or control signals, e.g., based upon user inputs received at user interface sensor 326 and/or remote control attachment 340, to be communicated to console 100 such that console 100, in turn, can power and/or control surgical device 200 (FIGS. 1 and 3) and/or pump 600 based thereon. Feedback signals from sensor data obtained at remote control attachment 340 and control signals based upon user inputs to remote control attachment 340 are detailed below. In aspects where cassette 230 includes one or more flow sensors 329, feedback signals from flow sensor(s) 329 can be communicated to console 100 to enable determination of whether there is a blockage or other error, e.g., in a situation where no fluid flow or insufficient fluid flow through the fluid line 612 is detected by flow sensor 329 despite pump 600 being activated from console 100 to pump fluid along that fluid line 612 or where, despite fluid flow not being activated through fluid line 612 via console 100, fluid flow therethrough is detected by flow sensor 329, thus indicating a defective valve or valve actuator.

With respect to control signals from user interface sensor 326, when a user input to eject the cassette, e.g., a particular contact, force, pattern, etc. input to user interface sensor 326, is sensed at user interface sensor 326, a signal is communicated from user interface sensor 326 to I/O 335 and relayed to processor 336 which, in turn, directs a corresponding signal to be wirelessly communicated from electronics board 330 to electronics board 180 to notify application processor 186 of console 100 that an ejection command has been received. In response to this ejection command, application processor 186 may, for example, provide a control signal to first portion 610 of pump 600 to disengage from second portion 620 of pump, e.g., releasing or retracting actuators and/or other components associated with first portion 610 of pump 600, thereby facilitating withdrawal of cassette 320 from cassette bay 170.

Turning to FIGS. 5 and 7-9, remote control attachment 340, as noted above, is electrically connected to cassette 320 (and, more specifically, electronics board 330 thereof) via electrical connector 360. Remote control attachment 340 includes a flexible base 342 including a releasable connector 344, a flexible circuit board 346 supported on flexible base 342, an inertial measurement sensor 348 disposed on flexible circuit board 346, a user input interface 350 disposed on flexible circuit board 346, and an output device 352 disposed on flexible circuit board 346.

Flexible base 342, as noted above, supports flexible circuit board 346 thereon. Releasable connector 344 of flexible base 342 may include, for example, an adhesive layer (with a peelable backing layer) configured to enable releasable adhesion of remote control attachment 340 to handpiece 210 of surgical device 200. Alternatively or additionally, releasable connector 344 may include a clip configured to snap-fit about at least a portion of handpiece 210 of surgical device 200 to releasably attach remote control attachment 340 thereto. Other features enabling releasable attachment of remote control attachment 340 on handpiece 210 of surgical device 200 are also contemplated. Regardless of the particular configuration of releasable connector 344, the flexibility of flexible base 342 and flexible circuit board 346 enable remote control attachment 340 to conform to handpiece 210 of surgical device 200 so as not to disrupt the ergonomics thereof. Further, the flexibility of flexible base 342 and flexible circuit board 346 enable remote control attachment 340 to be positioned at various locations on handpiece 210, e.g., based upon user preference, and/or to releasably engage various handpieces of different size, shape, or other configuration.

Inertial measurement sensor 348 may include, for example, one or more accelerometers, one or more gyroscopes, one or more magnetometers, combinations thereof, etc. In aspects, inertial measurement sensor 348 includes at least one of a 3D accelerometer, 3D gyroscope, or 3D magnetometer and, in aspects, includes an inertial measurement unit (IMU) having two or more of the 3D accelerometer, 3D gyroscope, or 3D magnetometer. The 3D accelerometer is configured to sense linear acceleration (m/s$^2$), tilt, tap, shock, free fall, and vibration. The 3D gyroscope is configured to sense angular rate (degree/s). The 3D magnetometer is configured to sense magnetic field (gauss). Using these inputs, the sensor 348 (or IMU, where provided) is capable of one or more of: tracking orientation of handpiece 210, tracking movement of handpiece 210 in 3D space, and/or detecting activation and deactivation of handpiece 210, e.g., motor start/stop conditions. Other suitable inertial measurement sensors are also contemplated.

Based on sensor data received by console 100 from inertial measurement sensor 348 (via the wired or wireless communication interface between console 100 and fluid cassette and remote control assembly 300), console 100 may confirm that handpiece 210 was activated and/or deactivated properly (e.g., by comparing the control signals output to surgical device 200 from console 100 with motor start/stop conditions detected). Additionally or alternatively, console 100 may determine which handpiece 210 among a plurality of handpieces is the active handpiece (e.g., based on accelerometer and/or gyroscope data indicating the moving handpiece) and correspondingly assign functions, auxiliary devices, fluid lines, etc. thereto while deactivating the inactive handpieces.

Sensor data from inertial measurement sensor 348 may also be utilized to determine an orientation of handpiece 210 from one or more to one or more predefined orientations, e.g., at or sufficiently close (within 10 degrees or within 20 degrees) to one of the predefined orientations. The predefined orientations may be set at manufacturing, may be user-settable, or may be determined in any other suitable manner. The predefined orientations may include, for example, a use orientation (wherein handpiece 210 is angled with the tip facing down, indicating active use), a change orientation (wherein handpiece 210 is vertically upwardly oriented, indicating an intent to change out a tool), or a standby orientation (wherein handpiece 210 is horizontally oriented indicating handpiece 210 is resting on a surgical tray). When the active mode is detected, console 100 may maintain assign functions, auxiliary devices, fluid lines, etc. to handpiece 210. When the change mode is detected, console 100 may inhibit activation to protect the patient and clinicians. When the standby orientation is detected, console 100 may switch handpiece 210 to a safe mode to prevent inadvertent activation thereof.

The sensed data from inertial measurement sensor 348 may additionally or alternatively be utilized to determine a trajectory of motion of handpiece 210, e.g., based upon tracking position and orientation as a function of time, and monitor the trajectory thereof. Once the trajectory of handpiece 210 is determined, further motion thereof is monitored and compared to the determined trajectory. If the further motion is aligned with the determined trajectory, sufficiently close to the determined trajectory (such as, for example, within a cone of deviation or other acceptable limits), or otherwise acceptable based on the determined trajectory, no output or a confirmatory output, e.g., illuminating the output device 352 green, is provided. On the other hand, if the further motion sufficiently deviates from the determined trajectory or otherwise exceeds acceptable limits, a suitable output warning the clinician may be provided, e.g., illuminating the output device 352 flashing red and/or outputting a warning tone from output device 352. In this manner, a clinician is alerted as to whether handpiece 210 is maintaining its trajectory or if handpiece no longer follows the determined trajectory thereof, e.g., is off trajectory. In addition to as an alternative to trajectory monitoring, movement may be tracked to detect unexpected motions that would not typically occur (or have not typically occurred) and, thus, could warn the clinician regarding the same. The motion and/or trajectory monitoring may be performed at console 100 (via the wireless communication between console 100 and fluid cassette and remote control assembly 300).

User input interface 350 of remote control attachment 340 is configured as a finger input device such as, for example, a keypad, D-pad, capacitive surface, resistive surface, or other suitable user input sensor configured to sense a contact and/or force input, e.g., from one or more fingers of a clinician. Depending upon the location(s) of the inputs to user input interface 350, the length of input, the number of inputs, the pattern of inputs (such as, for example, a particular finger gesture), and/or other distinguishable input actions, different functions can be provided. For example, different inputs may be configured to, for example and without limitation: activate/deactivate handpiece 210; switch between different modes of operation; increase/decrease the speed of the motor of handpiece 210; start/stop fluid flow; increase/decrease the rate of fluid flow' switch fluid flow paths, etc. In aspects, the particular inputs may be preset (at manufacturing) or the clinician may assign particular functions to particular inputs. Regardless of the particular input configuration, the inputs received at user input interface 350 are relayed to console 100 (via the wireless communication between console 100 and fluid cassette and remote control assembly 300) to enable console 100 to control surgical device 200, pump 600, and/or any other components based thereon and/or to provide suitable outputs base thereon.

Output device 352 of remote control attachment 340 may include, for example, one or more LED's or other suitable visual indicator outputs and/or a speaker or other suitable audio indicator output. Thus, depending upon an operating mode, fluid flow condition, detected error, etc., a visual and/or audible output may be provided to the clinician at handpiece 210, thus obviating the need for the clinician to turn back to console 100. Providing an output at handpieces 210 also enables the indication to be provided in close proximity to the clinician and, thus, such that the indication can be more readily perceived. It is noted that output device 352 need not only provide indication outputs relating to remote control attachment 340 or cassette 320 but, rather, may receive signals from console 100 (via the wireless communication between console 100 and fluid cassette and remote control assembly 300) for output at handpiece 210.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. A fluid cassette and remote control assembly, comprising:
   a cassette including at least one fluid line configured to operably couple between at least one fluid input and at least one fluid output, the cassette configured to operably couple to a console to enable pumping of fluid along the at least one fluid line, the cassette including an electronics board configured to communicate with the console when the cassette is engaged with the console;
   a remote control attachment configured to releasably attach to a handpiece of a surgical device, the remote control attachment including at least one of: a sensor configured to sense a property of the handpiece, a user input interface configured to receive an input from a clinician, or an output device configured to output an indicator to a clinician; and
   an electrical connector connecting the remote control attachment with the cassette, thereby electrically coupling the electronics board of the cassette with the at least one of the sensor, the user input interface, or the output device of the remote control attachment,
   wherein the electronics board is configured to wirelessly receive power from the console to power the electronics board and the remote control attachment.

2. The fluid cassette and remote control assembly according to claim 1, wherein the sensor is an inertial measurement sensor.

3. The fluid cassette and remote control assembly according to claim 2, wherein the inertial measurement sensor includes at least one of an accelerometer configured to sense movement of the handpiece, a gyroscope configured to sense orientation of the handpiece, or a magnetometer configured to sense activation of the handpiece.

4. The fluid cassette and remote control assembly according to claim 1, wherein the user input interface is configured to sense a finger gesture input to a surface thereof.

5. The fluid cassette and remote control assembly according to claim 4, wherein the user input interface is configured to receive a finger gesture input on the surface thereof to control at least one of operation of the surgical device or pumping of the fluid along the at least one fluid line via the communication between the electronics board and the console.

6. The fluid cassette and remote control assembly according to claim 1, wherein the output device is configured to provide at least one of an audible output or a visual output.

7. The fluid cassette and remote control assembly according to claim 6, wherein the output device is configured to provide an output generated by the console and communicated to the remote control attachment via the communication between the electronics board and the console.

8. The fluid cassette and remote control assembly according to claim 1, wherein the remote control attachment includes each of: the sensor, the user input interface, and the output device.

9. The fluid cassette and remote control assembly according to claim 1, wherein the cassette further includes a user input sensor disposed thereon and electrically connected to the electronics board for relaying sensed user inputs to the console via wireless communication between the electronics board and the console.

10. The fluid cassette and remote control assembly according to claim 9, wherein, in response to the user input sensor sensing a user input, the electronics board wirelessly sends an eject cartridge signal to the console.

11. The fluid cassette and remote control assembly according to claim 1, further comprising tubing connected to the at least one fluid output at a first end and configured to connect to the surgical device at a second end, wherein the tubing and the electrical connector are bundled with one another along portions of lengths thereof.

12. A surgical system, comprising:
   a console including at least one surgical device port and at least one cassette bay, the console including a first electronics board and pump components operably positioned relative to the at least one cassette bay;
   a surgical device configured to connect to the console via the at least one surgical device port, the surgical device including a handpiece and an end effector; and
   a fluid cassette and remote control assembly, including:
      a cassette configured for receipt within the at least one cassette bay, the cassette including a second electronics board and at least one fluid line configured to operably couple between at least one fluid input and at least one fluid output, wherein, when the cassette is received within the at least one cassette bay, the cassette is configured to operably couple to the pump components of the console to enable pumping of fluid along the at least one fluid line and the first and second electronics boards are configured to communicate with one another;
      a remote control attachment configured to releasably attach to the handpiece of the surgical device, the remote control attachment including at least one of: a sensor configured to sense a property of the handpiece, a user input interface configured to receive an input from a clinician, or an output device configured to output an indicator to a clinician; and an electrical connector connecting the remote control attachment with the cassette to electrically couple the second electronics board with the at least one of the sensor, the user input interface, or the output device, thereby coupling the first electronics board with the at least one of the sensor, the user input interface, or the output device when the cassette is received within the at least one cassette bay, wherein the cassette further includes a user input sensor disposed thereon and electrically connected to the second electronics board for relaying sensed user inputs to the console via the communication between the first and second electronics boards, and wherein, in response to the user input sensor sensing a user input, the second electronics board sends an eject cartridge signal to the first electronics board to disengage the pump components of the console.

13. The system according to claim 12, wherein the sensor is an inertial measurement sensor including at least one of an accelerometer configured to sense movement of the handpiece, a gyroscope configured to sense orientation of the handpiece, or a magnetometer configured to sense activation of the handpiece.

14. The system according to claim 12, wherein the user input interface is configured to receive a finger gesture input on a surface thereof to control at least one of operation of the surgical device or pumping of fluid along the at least one fluid line via the communication between the first and second electronics boards.

15. The system according to claim 12, wherein the output device is configured to provide at least one of an audible output or a visual output generated by the console and communicated to the remote control attachment via the communication between the first and second electronics boards.

16. The system according to claim 12, wherein the first electronics board is configured to wirelessly transfer power to the second electronics board to power the second electronics board and the remote control attachment.

17. The system according to claim 12, further comprising tubing connected to the at least one fluid output at a first end and configured to connect to the surgical instrument at a second end, wherein the tubing and the electrical connector are bundled with one another along portions of lengths thereof.

18. A fluid cassette and remote control assembly, comprising:

a cassette including at least one fluid line configured to operably couple between at least one fluid input and at least one fluid output, the cassette configured to operably couple to a console to enable pumping of fluid along the at least one fluid line, the cassette including an electronics board configured to communicate with the console when the cassette is engaged with the console;

a remote control attachment configured to releasably attach to a handpiece of a surgical device, the remote control attachment including at least one of: a sensor configured to sense a property of the handpiece, a user input interface configured to receive an input from a clinician, or an output device configured to output an indicator to a clinician; and an electrical connector connecting the remote control attachment with the cassette, thereby electrically coupling the electronics board of the cassette with the at least one of the sensor, the user input interface, or the output device of the remote control attachment, wherein the cassette further includes a user input sensor disposed thereon and electrically connected to the electronics board for relaying sensed user inputs to the console via wireless communication between the electronics board and the console, and wherein, in response to the user input sensor sensing a user input, the electronics board wirelessly sends an eject cartridge signal to the console.

* * * * *